(12) United States Patent
Qin et al.

(10) Patent No.: US 6,706,944 B2
(45) Date of Patent: Mar. 16, 2004

(54) ABSORBENT MATERIALS HAVING IMPROVED ABSORBENT PROPERTIES

(75) Inventors: Jian Qin, Appleton, WI (US); Xiaomin Zhang, Appleton, WI (US); Sridhar Ranganathan, Suwanee, GA (US); Yong Li, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 90 days.

(21) Appl. No.: 10/017,465

(22) Filed: Dec. 14, 2001

(65) Prior Publication Data

US 2003/0139717 A1 Jul. 24, 2003

(51) Int. Cl.[7] ................................................. A61F 13/15
(52) U.S. Cl. .................... 604/367; 604/365; 604/366
(58) Field of Search ................................ 604/367, 365, 604/366, 369, 370, 372, 377; 428/304.4, 311.11, 311.71, 316.6, 317.1, 407, 452; 521/64, 84.1, 141, 149, 182

(56) References Cited

U.S. PATENT DOCUMENTS

| | | | |
|---|---|---|---|
| 4,127,547 A | 11/1978 | Smarook | |
| 4,179,540 A | 12/1979 | Smarook | |
| 4,394,930 A | 7/1983 | Korpman | |
| 4,410,571 A | 10/1983 | Korpman | |
| 4,559,243 A | 12/1985 | Pässler et al. | |
| 4,758,466 A | 7/1988 | Dabi et al. | |
| 5,149,335 A | 9/1992 | Kellenberger et al. | |
| 5,252,619 A | 10/1993 | Brownscombe et al. | |
| 5,268,224 A | 12/1993 | DesMarais et al. | |
| 5,290,820 A | 3/1994 | Brownscombe et al. | |
| 5,300,054 A | 4/1994 | Feist et al. | |
| 5,304,161 A | 4/1994 | Noel et al. | |
| 5,328,935 A | 7/1994 | Van Phan et al. | |
| 5,334,621 A | 8/1994 | Beshouri | |
| 5,338,766 A | 8/1994 | Phan et al. | |
| 5,358,974 A | 10/1994 | Brownscombe et al. | |
| 5,364,382 A | 11/1994 | Latimer et al. | |
| 5,372,877 A | 12/1994 | Kannankeril | |
| 5,439,458 A | 8/1995 | Noel et al. | |
| 5,490,846 A | 2/1996 | Ellis et al. | |
| 5,509,915 A | 4/1996 | Hanson et al. | |
| 5,550,167 A | 8/1996 | DesMarais | |
| 5,563,179 A | 10/1996 | Stone et al. | |
| 5,571,849 A | 11/1996 | DesMarais | |
| 5,573,994 A | 11/1996 | Kabra et al. | |
| 5,601,542 A | 2/1997 | Melius et al. ................ 604/368 |

(List continued on next page.)

FOREIGN PATENT DOCUMENTS

| | | | |
|---|---|---|---|
| WO | 86/03505 | 6/1986 | |
| WO | 99/61518 | 12/1999 | |
| WO | WO 00/38610 | 7/2000 | ........... A61F/13/15 |
| WO | 00/78369 | 12/2000 | |
| WO | WO 01/13843 A1 | 3/2001 | ........... A61F/13/15 |
| WO | WO 02/49565 A2 | 6/2002 | ........... A61F/13/53 |

Primary Examiner—Weilun Lo
Assistant Examiner—Jacqueline F. Stephens
(74) Attorney, Agent, or Firm—Pauley Petersen & Erickson

(57) ABSTRACT

An absorbent fibrous foam composite comprising a fluid intake capacity of at least 15 g/g, a vertical wicking distance of at least 10 cm, and an absorbency under zero load of at least 15 g/g. The absorbent fibrous foam composite comprising a water insoluble fibrous material and a superabsorbent material. The absorbent fibrous foam composite made by forming a slurry of water, a water-insoluble fiber, and a binding agent. A water-swellable, water-insoluble superabsorbent material is added to the slurry and the temperature is lowered until the water freezes. The frozen water is then removed by sublimation process and an absorbent fibrous foam recovered. The Gelation Time, which represents a fluid absorption rate of superabsorbent during the preparation, is critical to preparing uniform absorbent freeze-dried foams and can be adjusted by various mixing conditions and physical and chemical superabsorbent treatments.

83 Claims, 6 Drawing Sheets

U.S. PATENT DOCUMENTS

| | | |
|---|---|---|
| 5,612,385 A | 3/1997 | Ceaser et al. |
| 5,632,737 A | 5/1997 | Stone et al. |
| 5,651,862 A | 7/1997 | Anderson et al. |
| 5,692,939 A | 12/1997 | DesMarais |
| 5,733,272 A | 3/1998 | Brunner et al. |
| 5,750,585 A * | 5/1998 | Park et al. .................. 521/143 |
| 5,763,067 A | 6/1998 | Brüggemann et al. |
| 5,763,499 A | 6/1998 | DesMarais |
| 5,786,395 A | 7/1998 | Stone et al. |
| 5,795,921 A | 8/1998 | Dyer et al. |
| 5,843,063 A | 12/1998 | Anderson et al. |
| 5,849,805 A | 12/1998 | Dyer |
| 5,851,648 A | 12/1998 | Stone et al. |
| 5,851,672 A | 12/1998 | Wang et al. |
| 5,869,171 A | 2/1999 | Shiveley et al. |
| 5,873,869 A | 2/1999 | Hammons et al. |
| 5,899,893 A | 5/1999 | Dyer et al. |
| 5,904,675 A | 5/1999 | Laux et al. |
| 5,948,829 A | 9/1999 | Wallajapet et al. |
| 5,985,432 A | 11/1999 | Wang et al. |
| 5,985,434 A | 11/1999 | Qin et al. |
| 6,019,871 A | 2/2000 | Rökman et al. |
| 6,027,795 A | 2/2000 | Kabra et al. |
| 6,033,769 A | 3/2000 | Brueggemann et al. |
| 6,071,580 A | 6/2000 | Bland et al. |
| 6,083,211 A | 7/2000 | DesMarais |
| 6,103,358 A | 8/2000 | Brüggemann et al. |
| 6,261,679 B1 | 7/2001 | Chen et al. |
| 6,294,710 B1 * | 9/2001 | Schmidt et al. ............. 604/378 |

\* cited by examiner

500um 3kv 10x

ABSORBENT MATERIALS HAVING IMPROVED ABSORBENT PROPERTIES

FIELD OF THE INVENTION

This invention relates to absorbent materials having improved multifunctional absorbent properties. More specifically this invention relates to absorbent fibrous composites having rapid fluid intake, improved fluid distribution, and high saturation capacity. This invention also relates to a process for making the absorbent materials.

BACKGROUND OF THE INVENTION

Various absorbent materials and structure are known in the art. Important characteristics of commercial absorbent materials and structures include fluid intake, fluid retention, and fluid distribution. Known absorbent materials and structures often exhibit at most two of these desired characteristics and are weak in the others. Nonwoven surge materials, as taught in U.S. Pat. No. 5,490,846 to Ellis et al. and in U.S. Pat. No. 5,364,382 to Latimer, for example, have excellent intake functionality but almost no fluid distribution and retention properties. Uncreped through air-dried tissue (UCTAD) material, typically a tissue made from natural fibers such as wood pulp, has a high density providing superior fluid distribution capabilities but poor fluid intake and retention. Current diaper absorbent cores comprising an absorbent fluff and superabsorbent material combination provide good fluid absorbency but, depending on the core density, poor fluid intake and/or distribution. A higher density absorbent core improves distribution but sacrifices fluid intake but a low density absorbent core improves fluid intake and sacrifices distribution.

A typical disposable absorbent product generally has a composite structure including a topsheet, a backsheet, and an absorbent structure between the topsheet and backsheet. In current commercial absorbent structures layers of different materials, such as a surge layer and an absorbent core layer, are required to provide desired fluid handling characteristics. The result is a bulky absorbent article with many production steps and high cost. There is a need for an absorbent material having combined rapid fluid intake, increased fluid retention, and efficient fluid distribution characteristics.

The use of water-swellable, water-insoluble superabsorbent materials in a fibrous matrix as an absorbent core is well known in the art. As an alternative to superabsorbent containing fibrous matrix absorbent cores, absorbent foams are also known. Absorbent foams generally have lower absorbency rates and can have poor liquid distribution properties. This is typically due to physical characteristics of the foam structure, including discontinuous pore channels, a too large average cell size, unacceptably wide cell size distribution, and/or capillary diameters that vary widely and randomly.

U.S. Pat. No. 6,261,679, issued Jul. 17, 2001 to Chen et al. teaches absorbent fibrous structure that are foam-like, wherein the structure is primarily composed of hydrophilic fibers which serve in part as struts between the open cells. The fibrous structure provides many significant benefits. However, lack of significant amounts of superabsorbent materials in the absorbent structures of U.S. Pat. No. 6,261,679 leaves a need for improved, more absorbent fibrous structures.

There is a need for an absorbent structure having rapid fluid intake, increased fluid retention, and efficient fluid distribution characteristics.

SUMMARY OF THE INVENTION

This invention relates to absorbent fibrous foam composites having improved fluid handling properties and methods of making the absorbent fibrous foams. The absorbent fibrous foam composites of one embodiment of this invention have a fluid intake capacity of at least 15 g fluid/g composite, a vertical wicking distance of at least 10 cm, and an absorbency under zero load value of at least 15 grams fluid per gram composite. The absorbent fibrous foam composites of another embodiment of this invention have an intake rate of at least 1.9 cc liquid/second at 80% composite saturation and a liquid lockup fraction of at least about 0.75 at 50% superabsorbent saturation.

The low-density absorbent fibrous foam composites of one embodiment of this invention include a water-insoluble fiber and a superabsorbent material. The superabsorbent material has a weight amount between about 10 to 70 weight percent and the water-insoluble fiber has a weight amount between about 20 to 80 weight percent, wherein weight percent is based on total weight of the absorbent composite.

The low-density absorbent fibrous composite of one embodiment of this invention includes a water insoluble fiber, a superabsorbent material, and a binding agent. The binding agent constitutes about 0 to 10 weight percent, based on total weight of the absorbent composite. The binding agent is used to bind the fibers together and provides excellent wet and dry strength. In one embodiment the superabsorbent material can also act as a binding agent.

One embodiment of the invention is a freeze-dried absorbent fibrous foam. The freeze-dried absorbent fibrous foam is made by forming a slurry comprising water, a water-insoluble fiber, and a binding agent. An absorbent material having a slow absorption time, or a surface treated fast absorption material, is then added to the slurry. The slurry has to be formed into a uniform sheet while enough interstitial fluid is still present or the slurry is still flowable. The slurry is cooled to a temperature between about −50° C. and 0° C. at a cooling rate effective to freeze the water. The frozen water is removed through sublimation and a fibrous absorbent foam is recovered.

DEFINITIONS

Figure 1:
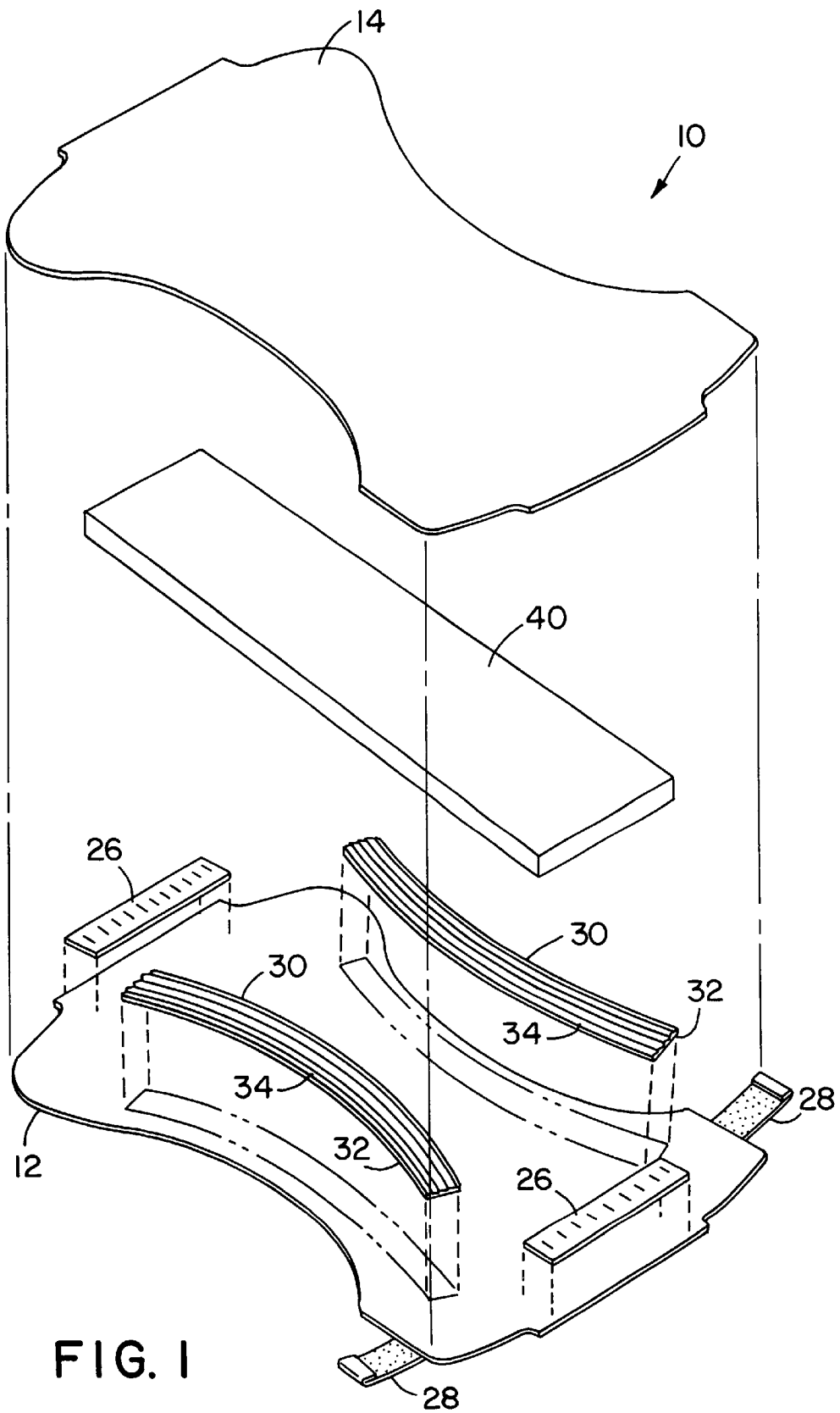
FIG. 1 is an exploded perspective view of a diaper according to one embodiment of this invention.

Within the context of this specification, each term or phrase below will include the following meaning or meanings.

"Foam" refers to two-phase gas-solid systems that have a supporting solid lattice of cell walls that are continuous throughout the structure. The gas, typically air, phase in a foam is usually distributed in void pockets often called cells. "Open-cell foams" are polymeric materials having substantial void space in the form of cells defined by a plurality of mutually connected, three dimensionally branched webs of polymeric material. The cells typically have openings to permit fluid communication from one cell to another. In other words, the individual cells of the foam are not completely isolated from each other by the polymeric material of the cell walls. The cells in such substantially open-celled foam structures have intercellular openings which are large enough to permit fluid transfer from one cell to another within the foam structure. For purposes of this invention, a foam material is "open-celled" if at least 80% of the cells in the foam structure that are at least about 1 micron size are in fluid communication with at least one adjacent cell.

"Capillary size" refers to size of the open cells in the fibrous composites of this invention. The capillaries, or interconnected open cells, are the passage ways through which fluids are taken into the absorbent fibrous composites.

An absorbent fibrous composite is "flexible" if it meets a modified flexibility test based on the flexibility tests for various foams provided by the American Society for Testing and Materials (ASTM). Specifically, a flexible foam is one that does not rupture when a 20×2.5×2.5 cm piece is wrapped around a 2.5 cm mandrel at a uniform rate of 1 lap/5 seconds at 20° C. "Rigid" foams are those which rupture in the above-mentioned test. Absorbent fibrous composites of the present invention can be either flexible or rigid, with flexible absorbent fibrous composites being desirable in certain absorbent articles.

"Vertical Liquid Flux" refers to the liquid flux value of the sample strip measured by the vertical wicking test at a particular height. The value is calculated by dividing the grams of liquid absorbed by the sample strip by each of: the basis weight, in grams per square meter, of the sample strip; the time, in minutes, needed by the liquid to reach the particular height; and the width, in inches, of the sample strip.

"Low-density absorbent composite" refers to an absorbent composite having a density less than 0.1 gram per cubic centimeter.

"Hydrophilic" describes fibers or the surfaces of fibers which are wettable by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

"Superabsorbent material" refers to a water-swellable, water-insoluble organic or inorganic material capable, under the most favorable conditions, of absorbing at least about 10 times its weight, preferably at least about 20 times its weight in an aqueous solution containing 0.9% by weight sodium chloride. Superabsorbent material can comprise a form including particles, fibers, nonwovens, coforms, printings, coatings, other structural forms, and combinations thereof. "Water-swellable, water-insoluble" refers to the ability of a material to swell to a equilibrium volume in excess water but not dissolve into the water. The water-swellable, water-insoluble material generally retains its original identity or physical structure, but in a highly expanded state upon the absorption of water.

"Absorbency Under Load" (AUL) refers to the measure of the liquid retention capacity of a material under mechanical load. It is determined by a test which measures the amount, in grams, of a 0.9% by weight aqueous sodium chloride solution a gram of material can absorb in 1 hour under an applied load or restraining pressure of about 0.3 pound per square inch.

"Absorbency Under Zero Load (AUZL)" refers to the result of a test which measures the amount in grams of an aqueous 0.9% by weight sodium chloride solution that a gram of material can absorb in 1 hour under negligible applied load (about 0.01 pound per square inch). The test can be done as described above for the AUL test, except that the 100 g weight is not placed on the sample.

"Water-soluble" refers to materials which substantially dissolve in excess water to form a solution, thereby losing its initial form and becoming essentially molecularly dispersed throughout the water solution. As a general rule, a water-soluble material will be free from a substantial degree of crosslinking, as crosslinking tends to render a material water insoluble. A material that is "water insoluble" is one that is not water soluble according to this definition.

"Solvent" refers to a substance, particularly in liquid form, that is capable of dissolving a polymer used herein to form a substantially uniformly dispersed mixture at the molecular level.

The term "absorbent article" includes without limitation diapers, training pants, swim wear, absorbent underpants, baby wipes, adult incontinence products, feminine hygiene products, medical garments, underpads, bandages, absorbent drapes, and medical wipes, as well as industrial work wear garments.

These terms may be defined with additional language in the remaining portions of the specification.

DETAILED DESCRIPTION OF THE PRESENTLY PREFERRED EMBODIMENTS

This invention relates to absorbent composites comprising fibrous materials and superabsorbent materials. The absorbent composites exhibit multifunctional fluid absorbent properties such as increased retention, improved distribution and rapid fluid intake as well as having excellent softness and flexibility. The absorbent composites are useful in absorbent articles such as diapers, training pants, swim wear, adult incontinence articles, feminine care products, and medical absorbent products.

FIG. 1 illustrates an exploded perspective view of a disposable diaper. Referring to FIG. 1, disposable diaper 10 includes outer cover 12, body-side liner 14, and absorbent core 40 located between body-side liner 14 and outer cover 12. Absorbent core 40 can comprise any of the fibrous absorbent structures according to this invention. Body-side liner 14 and outer cover 12 are constructed of conventional non-absorbent materials. By "non-absorbent" it is meant that these materials, excluding the pockets filled with superabsorbent, have an absorptive capacity not exceeding 5 grams of 0.9% aqueous sodium chloride solution per gram of material.

Body-side liner 14 is constructed from highly liquid pervious materials. These layers function to transfer liquid from the wearer to absorbent core 40. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. U.S. Pat. No. 5,904,675, issued May 18, 1999 to Laux et al. and incorporated by reference, provides further examples of suitable surge materials. Either layer may also be an apertured plastic film. Suitable batting includes certain air formed thermochemical and chemithermomechanical wood pulps. The various layers of article 10 have dimensions which vary depending on the size and shape of the wearer.

Outer cover material 12 should be breathable to water vapor. Generally outer cover 12 will have a moisture vapor transmission rate (MVTR) of at least about 300 grams/$m^2$-24 hours, preferably at least about 1000 grams/$m^2$-24 hours, more preferably at least about 3000 grams/$m^2$-24 hours, measured using INDA Test Method IST-70.4-99, herein incorporated by reference.

Attached to outer cover 12 are waist elastics 26, fastening tapes 28 and leg elastics 30. The leg elastics 30 typically have a carrier sheet 32 and individual elastic strands 34. The diaper of FIG. 1 is a general representation of one basic diaper embodiment. Various modifications can be made to the design and materials of diaper parts.

Construction methods and materials of an embodiment of a diaper such as illustrated in FIG. 1, are set forth in greater detail in commonly assigned U.S. Pat. No. 5,509,915, issued Apr. 23, 1996 in the name of Hanson et al., incorporated herein by reference. Possible modifications to the diaper illustrated in FIG. 1 are set forth in commonly assigned U.S. Pat. No. 5,509,915 and in commonly assigned U.S. Pat. No. 5,364,382, issued Nov. 15, 1994 to Latimer et al.

According to one embodiment of this invention, the absorbent foam composite is a fluff based foam, referring to the fibrous material matrix of the absorbent foam structure. Absorbent fibrous foams according to one embodiment of this invention are freeze-dried absorbent fibrous foams comprising superabsorbent material. The method of making the freeze-dried absorbent foam of this invention includes forming a slurry of water, a binding agent, and a water insoluble fiber material. A water-swellable, water-insoluble superabsorbent material is then added to the slurry and the slurry is cooled to a temperature appropriate to freeze the water. The water is sublimated from the slurry, and a freeze-dried absorbent fibrous foam is recovered.

During the freeze drying process, the water molecules are first frozen at a temperature below the freezing point so that the slurry becomes an ice. After freezing the slurry, a high vacuum is applied on the frozen slurry. The vacuum is so high that it results in sublimation of water molecules from a solid state directly to a vapor state. Water vapor from the sublimation is collected by a condenser of a freeze dryer which is operated at a temperature of around −70° C. Freeze drying is typically a very slow process and it can take about 4 to 5 days to dry one batch of samples (about 4 pieces of absorbent foams originally containing about 8,000 g of water). Two parameters can be adjusted to control the drying rate: freeze drying temperature and vacuum. The freeze drying temperature can be between −60° C. to up to 0° C., temperatures at which a solution or slurry can still be maintained in solid state. The lower the freeze drying temperature, the slower the drying rate is, and vice versa. In general, fast drying rate causes a significant degree of shrinkage of absorbent foam due to high internal stress and lack of relaxation time. A lower slurry or solution concentration also causes a high degree of dimension reduction. High vacuum results in a fast drying rate. A high quality vacuum pump and a powerful condenser capable of reaching very low temperature (i.e., <−70° C.) are typically needed to achieve high vacuum. Using a condenser capable of reaching a low temperature helps ensure the capture of all moisture during sublimation of the frozen solution or slurry and thus achieves high vacuum.

High vacuum can also be achieved by lowering the freeze drying temperature. A lower drying temperature slows down the rate of sublimation, thus reducing the rate of moisture generation. High vacuum can be achieved by varying additional factors including without limitation, the concentration of a solution, consistency of a slurry, type of solvent, thickness of frozen solution/slurry sheet, batch load of solution or slurry, material ratio of absorbent to nonabsorbent (i.e., superabsorbent material to fibers), uniformity of a slurry, and combinations thereof.

Figure 4:
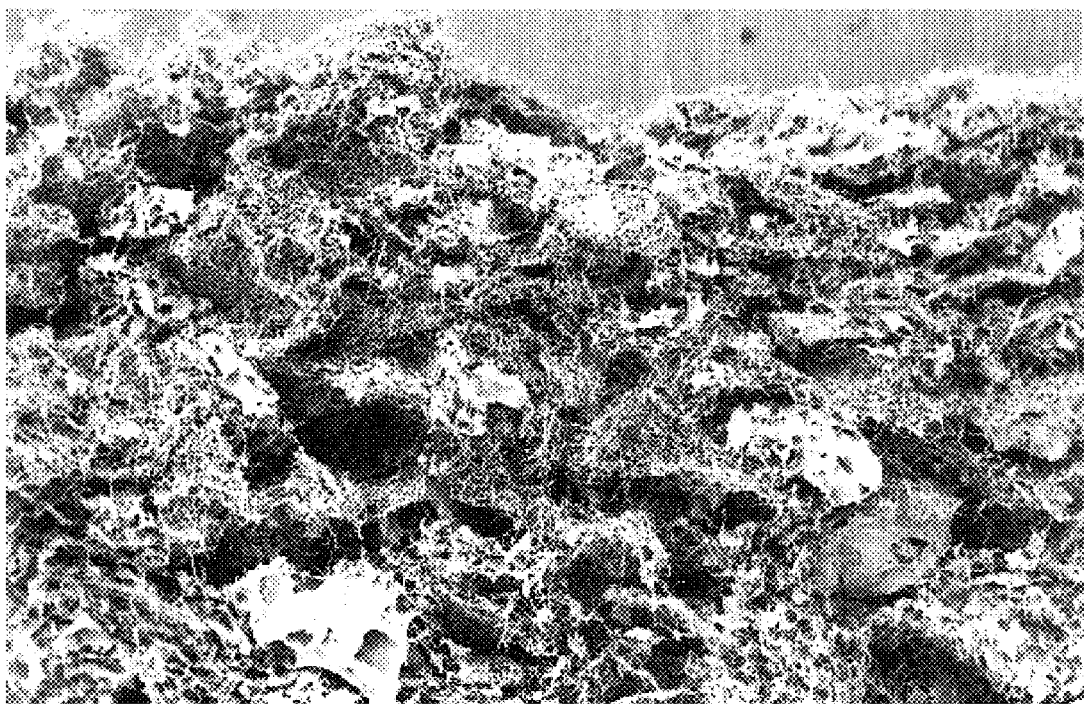
FIG. 4 is a photograph of a freeze-dried absorbent fibrous structure according to one embodiment of the invention.

The resulting foam, as shown in FIG. 4, is a soft absorbent foam including a water-swellable, water-insoluble superabsorbent polymer and a water insoluble fiber. The water-swellable, water-insoluble superabsorbent material is present in the absorbent fibrous foam in a weight amount of at least about 10% by weight, suitably between about 10% to 70% by weight, desirably between about 20% to 60% by weight, and more desirably between about 30% to 50% by weight. The water-insoluble fiber is present in the absorbent fibrous foam in a weight amount between about 10% to 90% by weight, suitably between about 20% to 80% by weight, and desirably between about 50% to 70% by weight. The binding agent is present in the absorbent fibrous foam in a weight amount between about 0% to 10% by weight, suitably between about 1% to 8% by weight, and desirably between about 2% to 5% by weight. The absorbent foam exhibits an absorbency under zero load value of at least 15 grams of liquid per gram of absorbent foam, a vertical wicking distance of at least 10 cm, and a fluid intake capability of at least 15 gram fluid per gram absorbent foam.

Water-insoluble fibers suitable for this invention include both natural fibers, including without limitation wood pulp and cotton linter, and synthetic fibers, including without limitation thermoplastic fibers, such as polyethylene fibers, polypropylene fibers, and poly(ethylene terephthalate) fibers, elastic fibers such as polyurethane fibers, and other synthetic fibers including, without limitation, polyvinyl alcohol, polyvinyl chloride, polyacrylonitrile, and combinations thereof. Hydrophilic fibers are preferred due to their wettability characteristics. Hydrophobic fibers can be used and are preferably treated with surfactants or other effective treatment to alter surface chemistry to increase wettability.

Fiber size directly affects capillary structure of the final foam. Generally, the larger the fiber size the larger the capillary size, and as the capillary size gets larger the wicking efficiency may decrease. Oppositely, smaller fiber size provides smaller capillary size but flux capacity may decrease. The fiber diameter is between about 1 $\mu$m to 100 $\mu$m, suitably between about 1 $\mu$m to 50 $\mu$m, and desirably between about 10 $\mu$m to 30 $\mu$m.

Water-swellable, water-insoluble superabsorbent materials suitable for this invention include crosslinked anionic and cationic polymers. Anionic polymer examples include without limitation, sodium-polyacrylate, carboxymethyl cellulose (CMC), carboxymethyl polysaccharides including starch, chitin, and other gums, polyaspartic acid salt, maleic anhydride-isobutylene copolymer, and copolymers and admixtures of these polymers. Cationic examples include without limitation, chitosan salts, polyquartemary ammonium salts, polyvinyl amines, and copolymers and admixtures of these polymers. Physical form of the superabsorbent materials can be particulate, fibrous, nonwoven, coform, printed, coated, combinations of these, or other forms.

Current commercial superabsorbent materials are generally characterized by rapid fluid absorbency. Adding these materials to the water-based slurry described above results in the superabsorbent materials absorbing the water from the slurry. This absorption results in undesired decrease in slurry flowability. When the slurry is used to form sheets of absorbent fibrous foam, the slurry is poured into a mold and a decrease in slurry flowability results in a non-uniform sheet of absorbent fibrous foam. A "uniform" sheet of foam refers to a sheet having substantially the same thickness and amount of superabsorbent material throughout the foam. Uniformity of the foam sheet can depend on the flowability of the slurry in that a flowable slurry will disperse uniformly in the foam production mold. A "non-uniform" foam sheet may have a varying thickness and/or component concentration throughout the foam sheet. A non-uniform sheet of absorbent fibrous foam usually contains many large cracks and voids which are detrimental to fluid distribution properties as well as dry and wet integrity. In order to retain flowability of the aqueous slurry a slow absorption rate superabsorbent material can be used, or the absorption rate of a fast absorption rate superabsorbent material may be slowed using external means. For example, suitable mixing conditions have been identified which slow down superabsorbent absorption rates.

Figure 2:
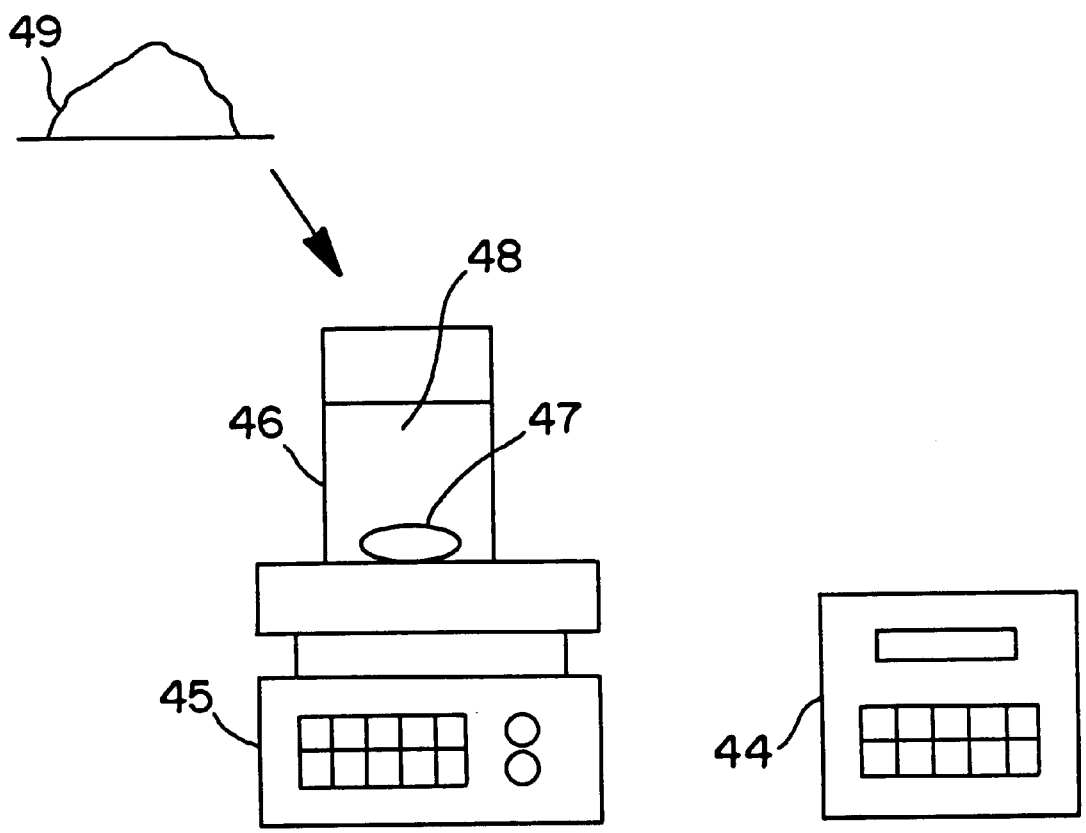
FIG. 2 is an illustration of the equipment for determining gelation time of superabsorbent material.

A parameter defined as Gelation Time (GT) is useful in determining if a superabsorbent material or mixing condition is suitable for this invention. FIG. 2 shows an apparatus usable in determining Gelation Time of a superabsorbent material. Beaker 46 is filled with distilled water 48 and placed on stir plate 45. Enough superabsorbent material 49, and any other agent if necessary, to absorb substantially all of water 48 is added to beaker 46. The slurry is stirred by magnetic stir bar 47 until the superabsorbent material absorbs almost all the water leaving a gelatinous material inside the beaker. It is important to emphasize that even a slow absorption rate superabsorbent material used in a freeze-dried absorbent composite will no longer exhibits slow absorption rate after the freeze drying process because of a significant increase in its surface area and internal void volume. The freeze-dried superabsorbent material particles after freeze-drying are analogous to popcorn in that there is an increased size/dimension and reduced density. Timer 44 records the time necessary for superabsorbent material 49 to absorb substantially all water 48. Suitable superabsorbent materials for this invention have a preferred Gelation Time greater than about 40 seconds, more suitably greater than 50 seconds, more suitably greater than 60 seconds, and desirably greater than 80 seconds.

A slow fluid absorption rate superabsorbent material can be achieved through many ways. Suitable ways include without limitation: (1) hydrophobilization of the superabsorbent material surface by coating the superabsorbent material with a hydrophobic agent such as a hydrocarbon oil or silicon oil, synthesizing superabsorbent beads in a hydrophobic medium such as benzene, or spinning superabsorbent fibers into a hydrophobic environment such as hot dry air; (2) reducing surface area of the superabsorbent material by using larger dimension superabsorbent particles or fibers; (3) using the nonionic, non-neutralized acid form of the superabsorbent material, which has a lower absorption rate, and then neutralizing to obtain desired superabsorbent salt while in the slurry solution; (4) encapsulating the superabsorbent materials in a slow liquid-penetrating film of slow absorbent or substantial nonabsorbent chemical such as polyvinyl alcohol which will break as the superabsorbent material begins to swell; and (5) using a non-neutralized ion exchanging superabsorbent that exhibits a slow absorption rate due to additional ion exchanging step, but is neutralized in the process of making the absorbent composite so that the neutralized superabsorbent material in the absorbent composite will exhibit a fast absorption rate.

It is important to emphasize that even if a slow absorption rate superabsorbent material is used in a freeze dried absorbent composite, the superabsorbent after the freeze drying process no longer exhibits a slow absorption rate because of a significant increase in surface area and internal void volume. The freeze dried superabsorbent particles appear like a popcorn-type of material with increased size/dimension and reduced density.

Suitable mixing conditions have also been discovered that slow down fast absorption rate superabsorbent material. Including a soluble, high molecular weight ionic polymer binding agent, such as carboxymethyl cellulose, into the slurry with the water-swellable, water-insoluble superabsorbent material slows the absorption rate of the superabsorbent material. The amount of high molecular weight ionic polymer has been found to be inversely proportional to absorption rate of the superabsorbent material. The change in viscosity of the slurry with the addition of the high molecular weight ionic polymer causes the slowed absorption rate. Therefore, when a proper amount of such water-soluble high molecular weight ionic polymer is used in the slurry prior to the addition of the superabsorbent material, absorption rate of the superabsorbent material becomes almost irrelevant to the formation of a uniform absorbent fibrous foam. Suitable high molecular weight ionic polymers have a molecular weight between about 10,000 to 10,000,000, desirably between about 50,000 to 1,000,000, and preferably between about 100,000 and 1,000,000.

Small amounts of organic solvents that are soluble in water but are not solvents to superabsorbent materials, such as methanol, ethanol, isopropanol, ethylene glycol, propylene glycol, ether, acetone, and/or mixtures of these, can be used in water to slow down absorption rate of superabsorbent materials. However, the solvents also reduce the superabsorbent material's swelling capability. It is important to limit the amount of such solvents to an extent that is enough to slow down absorption rate but not too much to significantly reduce swelling.

Temperature of the slurry also has an effect on the absorption rate of the superabsorbent material. Lowering the water temperature also slows the absorption rate of the superabsorbent material. The limit on lowering the temperature of the slurry water is near 0° C. in order to maintain the liquid state of the water. The temperature of the slurry is between about 0° C. to 23° C., suitably between about 4° C. to 15° C., and desirably between 4° C. and 10° C.

Figure 3:
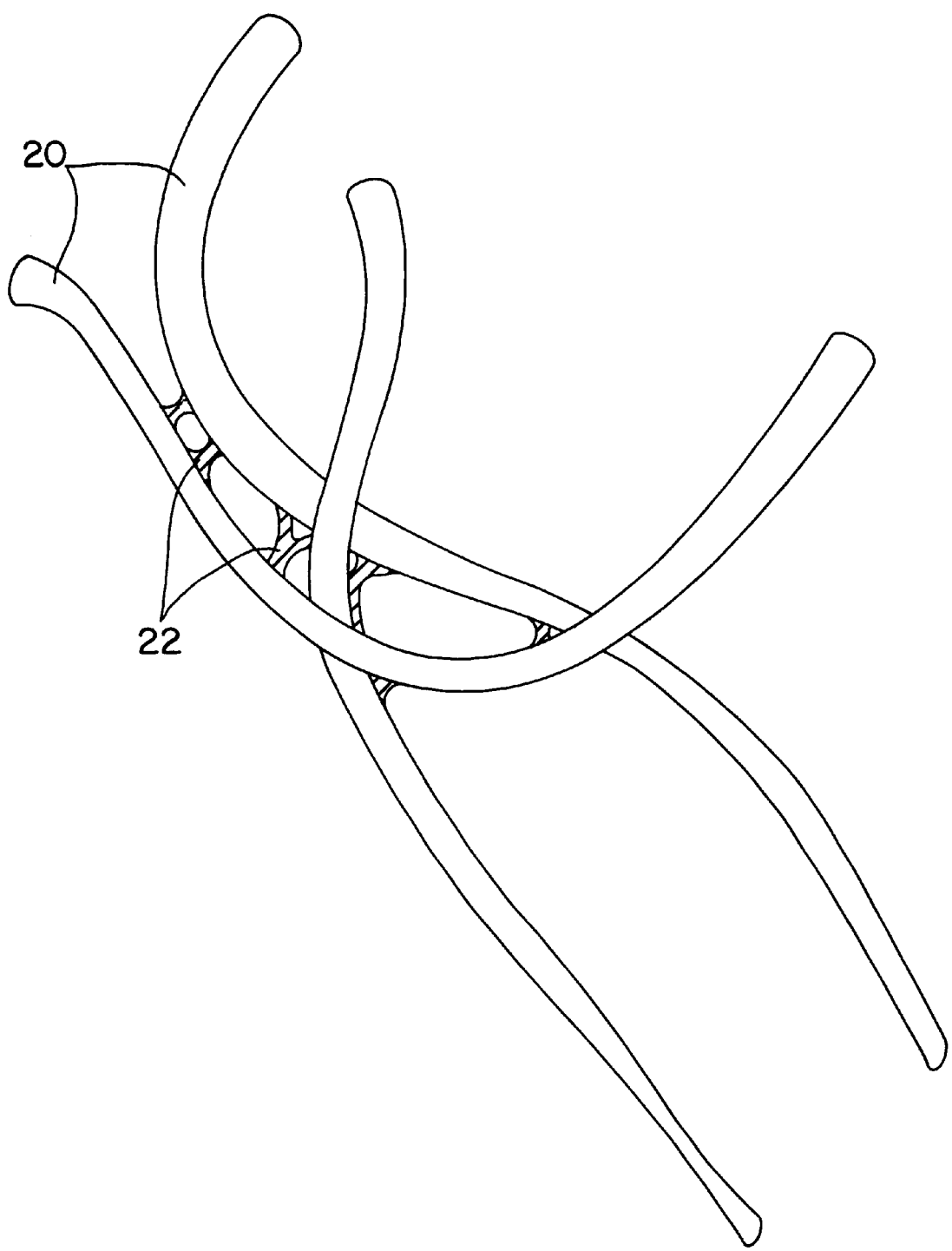
FIG. 3 depicts fibers in an absorbent structure according to one embodiment of this invention.

Binding agents provide strength to the absorbent fibrous foam both in the dry state and the wet state. Binding agents are typically water-soluble or dispersible in the slurry and water-insoluble in the absorbent fibrous foam after freeze-drying and/or heat curing. Binding agents bind the water-insoluble fibers and the superabsorbent materials together. As shown in FIG. 3, fibers 20 are held together in the fibrous absorbent foam structure by binding agent polymers 22. The binding agent may be water-swellable or not water-swellable. For use in absorbent articles the binding agent is preferably water-swellable. Preferred binding agent polymers are hydrophilic and substantially water-insoluble in the absorbent fibrous foam, providing desired wet strength of the fibrous composite.

For swellable binding agents, high molecular weight ionic polymers such as sodium-polyacrylate, carboxymethyl cellulose, and chitosan salt are useful in that they provide strength and absorbency to the freeze-dried foam. Other swellable binding agents include isobutylene-maleic anhydride copolymers, polyvinyl amines, polyquartemary ammoniums, polyvinyl alcohols, hydroxypropyl celluloses, polyethylene oxides, polypropylene oxides, polyethylene glycols, modified polysaccharides, proteins, and combinations thereof. Non-swellable, low molecular weight binding agents include kymene, latex, and other adhesives. Other non-swellable binding agents include any wet strength resins used in the paper making industries and any type of adhesive material. If an adhesive is used it is preferred that the adhesive is hydrophilic.

A crosslinking agent may be needed to insolubilize a water-soluble binding agent after formation of the absorbent foam structure. Crosslinking agents are typically water-soluble. Suitable crosslinking agents include organic compounds comprising at least two functional groups capable of reacting with at least one of carboxyl, carboxylic acid, amino, and/or hydroxyl groups. Examples of this type of crosslinking agents include without limitation, diamines, polyamines, diols, polyols, polycarboxylic acids, and polyoxides. Another suitable crosslinking agent is a metal ion with more than two positive charges, including without limitation, $Al^{3+}$, $Fe^{3+}$, $Ce^{3+}$, $Ce^{4+}$, $Ti^{4+}$, $Zr^{4+}$, and $Cr^{3+}$. When cationic polymer binding agents are used, polyanionic substances are suitable crosslinking agents. Polyanionic substances include without limitation, sodium-polyacrylate, carboxymethyl cellulose, and polymers including the phosphate anion $—PO_4^{3-}$.

In one embodiment of this invention the method of making a freeze-dried absorbent fibrous foams includes forming a slurry of water and a water insoluble fiber material with no binding agent. A water-swellable, water-soluble superabsorbent precursor is then added to the slurry and the slurry is cooled to a temperature appropriate to freeze the water. The water is removed from the slurry under high vacuum sublimation, and an absorbent fibrous foam is recovered.

When the water-soluble superabsorbent precursor is used, there is no need to add a binding agent. The superabsorbent material will act as the binding agent when the water-soluble superabsorbent precursor is crosslinked to form a water-swellable, water-insoluble network after foam production. The resulting foam is also a soft absorbent fibrous foam comprising a water-swellable, water-insoluble superabsorbent polymer and a water-insoluble fiber. The water-swellable, water-insoluble superabsorbent material is present in the absorbent fibrous foam in a weight amount of at least about 10% by weight, preferably between about 10% and 90% by weight, suitably between about 20% and 60% by weight, and desirably between about 30% and 50% by weight. The water-insoluble fiber is present in the absorbent fibrous foam in a weight amount between about 10% to 90% by weight, suitably between about 40% and 80% by weight, and desirably between about 50% and 70% by weight. The absorbent foam exhibits an absorbency under zero load value of at least 15 grams of liquid per gram of absorbent foam, a vertical wicking distance of at least 10 cm, and a fluid intake capacity of at least 15 grams liquid per gram absorbent foam.

Examples of water-soluble superabsorbent precursors include without limitation, polyacrylic acid, carboxymethyl cellulose, and chitosan salt. Examples of other superabsorbent precursors include isobutylene-maleic anhydride copolymers, polyvinyl amines, polyquartemary ammoniums, polyvinyl alcohols, hydroxypropyl celluloses, polyethylene oxides, polypropylene oxides, polyethylene glycols, modified polysaccharides, proteins, and combinations thereof.

When a superabsorbent precursor or a water-soluble binding agent is used in this invention a crosslinking agent is added. After the recovery of the freeze-dried fibrous foam the foam may require treatment to induce the crosslinking to provide a water-insoluble superabsorbent material or a water-insoluble binding agent. Suitable post foam treatment includes without limitation, heat curing at temperature greater than 60° C., ultraviolet radiation, microwave radiation, steam or high pressure, electronic beam radiation, organic solvents, and humidity treatment.

Suitable freezing temperature for making a freeze-dried fibrous foam is below the freezing point of the slurry solvent used. When water is used as the slurry solvent the temperature should be between about 0° C. and about –50° C., suitably between about –5° C. and –50° C., more suitably between about –10° C. and –40° C., and desirably between about –10° C. and –30° C. The selection of temperature is also dependent on the nature and concentration of the slurry. If the temperature selection is too close to the freezing point of the polymer slurry solution the frozen slurry may not have enough strength and may deform under vacuum removal of the solvent. If the temperature drops too far below the solvent freezing point the solvent molecules may form crystals which generally causes substantial cracks in the foam and reduces mechanical properties of the recovered foams.

While freezing the slurry it is important to control the cooling rate of the slurry from room temperature (~23° C.) to freezing temperature. The cooling rate should not exceed a critical cooling rate. "Critical cooling rate" refers to the cooling rate at which, or any rate greater, the slurry, as well as the final absorbent foam, begins to form visible cracks or visible non-uniformity. Critical cooling rate can vary depending upon the freezing point of the solvent used, concentration of slurry, use of a two solvent slurry, crystallizability of the solvent, ratio of insoluble fibers to superabsorbent material, and ratio of fibers to binding agent. A cooling rate slower than the critical cooling rate is preferred and generally results in a much more uniform pore structure and a softer, more flexible absorbent foam, due to the elimination of substantial cracks caused by uneven crystallization of solvent molecules. The cooling rate for an aqueous slurry having a weight ratio of insoluble fibers to soluble polymer less than 1 to 9 or a weight ratio of water-swellable superabsorbent material to water-soluble polymer less than 1 to 9, should be between about 0.01° C. and 10° C. per minute, suitably between about 0.05° C. to 3° C. per minute, and desirably between about 0.1° C. and 1° C. per minute.

Removal of the frozen solvent is preferably done by vacuum sublimation. Vacuum suitable for this invention is dependent on the volatility of solvent used. Higher vacuum can increase the rate of sublimation and lower vacuum applies a lower pressure on the frozen slurry that can result in less damage and a higher mechanical strength of the resulting foam. Vacuum conditions are desirably less than about 500 millitorrs, more suitably less than about 300 millitorrs, more suitably less than 200 millitorrs, and more suitably less than 100 millitorrs. In general, good vacuum can be achieved by either a good quality vacuum pump or a lower condenser temperature which captures more water vapor. Because sublimation is endothermic, the temperature of the frozen slurry is reduced as water is sublimated under vacuum. This means that the frozen slurry will be even colder and therefore it becomes more difficult to release water molecules. In order to compensate such energy loss, the freeze dryer should be equipped with a heater which provides just enough heat to compensate the energy loss to maintain temperature at a predetermined level.

Absorbent fibrous foam composites according to one embodiment of this invention exhibit high absorbency, excellent fluid distribution and intake, and excellent wet integrity, softness, and flexibility. The superabsorbent material provides the desired absorbent properties. Absorbent fibrous foam composites according one embodiment of this invention have an absorbency of at least about 15 grams liquid per gram of absorbent fibrous composite. Preferably the absorbency is at least 20 grams liquid per gram absorbent fibrous composite, and more preferably the absorbency is at least 25 grams liquid per gram absorbent fibrous composite.

The insoluble fibers of this invention provide the fibrous foam with an open pore structure in the fibrous absorbent composite. The open pore structure allows for rapid intake of fluid and excellent distribution of fluid. Pore size is determined by scanning electron microscopy. Absorbent fibrous foam composites of one embodiment of this invention have a pore size between about 0.1 and 1000 microns, suitably between about 1 and 300 microns, and desirably between about 5 and 100 microns.

Distribution of fluid is determined by vertical wicking height according to the vertical wicking height test explained below. Absorbent fibrous foam composites according to one embodiment of this invention have a vertical wicking height of at least about 10 cm. Desirably, the wicking height is at least about 15 cm.

Absorbent fibrous foam composites of one embodiment of this invention have enhanced fluid intake capacities. Absorbent fibrous foam composites of one embodiment of this invention have a fluid intake of at least about 15 grams fluid per gram absorbent composite. Desirably, the fluid intake is at least about 20 grams fluid per gram absorbent composite.

One embodiment of this invention is an absorbent fibrous foam composite having a high rate of liquid intake and a rapid liquid lock-up. Intake rate refers to the mass of liquid that is transferred into a absorbent fibrous foam composite as a function of time. The liquid may be present in the composite both as free liquid in the interstitial space and as liquid absorbed by the superabsorbent material. Liquid lock-up refers to the amount of liquid absorbed into the superabsorbent material within about 60 seconds of exposure. High lock-up fraction refers to a high percentage of liquid absorbed into the superabsorbent material. The combined benefits of high intake rate and high lock-up percentage result in an absorbent composite which can quickly contain a liquid insult and prevent that liquid from being expelled from the composite under pressure or gravity.

The freeze-dried absorbent foam composites of this invention have two unique absorbent properties which existing absorbent composites do not exhibit. The first unique absorbent property is excellent fluid distribution properties against gravity at a very low absorbent composite density. Absorbent composites of current commercial diaper products typically lose their fluid distribution ability against gravity when their densities are below 0.05 g/cc due to lack of capillary tension. Capillary tension of a porous matrix, such as in a fibrous absorbent composite, is inversely correlated to capillary size of open interconnected cavities. The smaller the capillary size, the higher the capillary tension, thus the higher the ability to move fluid against gravity. In current commercial absorbent composites, the low density is achieved at a cost of increasing capillary size and significantly reducing capillary tension. In the freeze-dried absorbent foam composites of this invention, a low density is achieved without increasing capillary size or reducing capillary tension, partly because of the physical structure of the superabsorbent material in the freeze dried foam. The superabsorbent material in the freeze-dried absorbent foam composites of this invention is in an almost or total fully swollen state, even though it holds little or no liquid, due to the absorption of fluid from the slurry during production and removal of that fluid by sublimation. Therefore, interfiber or interparticle capillary size remain small but overall density is significantly reduced. That is why the freeze-dried absorbent foam composites can exhibit a vertical wicking distance at least 10 cm at a density of less than 0.05 g/cc.

The second unique absorbent property is excellent fluid intake, even as density increases. Current commercial absorbent composites used in commercial diaper products can have a good fluid intake property at a low density. However, to increase fluid distribution and product integrity, current commercial absorbent composites generally have densities around about 0.2 g/cc. At a density of 0.2 g/cc, the fluid intake functions of the current absorbent composites are greatly compromised. Therefore, in diaper products a layer of low density material, such as nonwoven surge or curly cellulose fiber, is often used in combination with the absorbent composite to enhance fluid intake properties.

Freeze-dried fibrous foam composites of this invention, as-prepared, typically have a density below 0.1 g/cc. "As-prepared" refers to the freeze-dried foams produced according to this invention without additional densification. With a density below 0.1 g/cc, any material should have good fluid intake properties due to a relatively high volume of free space (i.e. voids and capillaries). Other fibrous materials are known to have a density below 0.1 g/cc, such as low density nonwoven surge materials and low density current commercial absorbent cores. However, such surge materials and absorbent cores generally lose the beneficial intake properties when they are densified to a density greater than 0.2 g/cc.

The freeze-dried absorbent foam composites of this invention have excellent fluid intake properties at any reasonable density. A freeze-dried foam absorbent composite of this invention is at a relatively low density. The freeze-dried foam absorbent composite can be densified to a density much higher than its "as-prepared" density, such as from 0.3 g/cc to 0.5 g/cc, by various physical compression means known in the art. The densified freeze-dried absorbent foam composites are beneficial in decreasing the overall thickness of absorbent articles. Densifying freeze-dried absorbent foam composites result in forming temporary inter-capillary bonds that hold composite at the higher density. The densified absorbent composite maintains essentially the same beneficial fluid intake properties (i.e., intake rate and capacity) as it had as a non-densified absorbent composite because a fluid insult releases the temporary inter-capillary bonds formed during the densification process. The breaking of the temporary inter-capillary bonds causes the densified absorbent composite to quickly expand back to at least substantially both the "as-prepared" shape and density in a matter of seconds. Such quick expansion allows the freeze dried absorbent composite to regain the fluid intake functionality it had at the initial, as-prepared lower density. Unless densified to a degree that permanent inter-capillary bonds formed by the binder are destroyed, the densification does not have a significant negative impact on fluid intake property of the freeze dried absorbent composite.

Freeze-dried foam composites of this invention (as-prepared) typically have a density below about 0.1 gram foam/cubic centimeter foam, suitably between about 0.01 g/cc and about 0.1 g/cc, or between about 0.01 g/cc and about 0.075 g/cc, or between about 0.01 g/cc and about 0.05 g/cc. Freeze-dried foams of this invention can be densified to obtain a density above about 0.2 g/cc, suitably between 0.2 g/cc to 0.5 g/cc. Densification of the freeze-dried absorbent composites also enhances overall softness and flexibility.

Freeze-dried absorbent foam composites according to one embodiment of this invention have a liquid intake of at least about 1.9 cubic centimeters/second at an absorbent composite saturation level of about 80%, and a liquid lock-up fraction of at least about 0.75 at about 50% superabsorbent saturation level. "Saturation level" refers to the amount of liquid absorbed divided by the total saturation capacity, or the total amount of liquid that can be absorbed. Additional fibrous absorbent composites having a liquid intake of at least about 1.9 cubic centimeters/second at an absorbent composite saturation level of about 80%, and a liquid lock-up fraction of at least about 0.75 at about 50% superabsorbent saturation level, as well as test methods for determining intake and lock-up, are disclosed in co-pending U.S. patent application, filed on Dec. 14, 2001, having Express Mail No. EL859245257US, herein incorporated by reference. Because intake rate and liquid lock-up fraction change as a function of saturation, the data will be normalized to a common set of criteria.

EXAMPLE 1

Several commercial superabsorbent materials (SAM) were measured by the Gelation Time test. The commercial superabsorbent materials tested were Drytech 2035 and Favor 880®. Drytech 2035 is a crosslinked partially neutralized sodium polyacrylate, commercially available from Dow Chemical Company of Midland, Mich., having a degree of neutralization around 70%. Favor 880 is a crosslinked partially neutralized sodium polyacrylate, commercially available from Stockhausen Inc. of Greensboro, N.C., having a degree of neutralization around 70%.

In addition, a polyacrylic acid superabsorbent material was also prepared for testing. The polyacrylic acid superabsorbent material was made by adding 24 kg of distilled water, 6 kg of acrylic acid, 10 grams of potassium persulfate ($K_2S_2O_8$), and 24 grams of N,N'-methylenebisacrylamide, all available from Aldrich Chemical Company, into a 10 gallon jacketed reactor equipped with an agitator and mixed at room temperature to form a completely dissolved solution. The reactor was then heated to 60° C. while running continuously for at least four hours. The resulting polyacrylic acid gel was cut into less than 1 inch cubes and dried in a ventilated oven at 60° C. for at least two days. The completely dried polyacrylic acid polymer was ground into particulate by a commercial grinder (Model: C.W. Brabender Granu-Grinder) and sieved using a Sweco Separator (24 inch Model), to obtain polyacrylic acid polymer in a size range of 150 to 850 microns. The polyacrylic acid polymers had a Absorbency Under Zero Load (AUZL) value of about 7 grams liquid per gram polymer and an AUL value of about 5 grams liquid per gram polymer. When the polyacrylic acid gel is mixed with sodium bicarbonate, $NaHCO_3$, powder at a ratio of about 55 weight % to 45 weight %, the mixture exhibits an AUZL of 32 grams liquid per gram mixture, and an AUL value of about 18 grams liquid per gram mixture.

To test the Gelation Time of the above superabsorbent materials, different amounts, as reported in Table 1, of CMC-7H, a carboxymethyl cellulose, available from Hercules Inc, were pre-dissolved as a binding agent into different beakers containing distilled water at 23° C. One superabsorbent material, Favor 880®, was also tested at additional water temperatures of 2° C., 42° C., and 63° C. An amount, as reported in Table 1, of the above superabsorbent materials was placed into the respective beaker and mixed. FIG. 2 is a diagram of the apparatus which was used to measure Gelation Time of the superabsorbent materials. To perform the test, 50 g of distilled water was added into a 100 ml Pyrex glass beaker. If a binding agent is needed for the test, add the agent into the water and make sure it is completely dissolved before a superabsorbent material is added into the beaker. The beaker is on the top of a magnetic stirrer (Dataplate© Digital Hot Plate/Stirrer, PMC-731, PMC Industries, Inc.) and the water mixture was stirred by a magnetic stir bar (1 inch long by ⅜ inch diameter) at a speed of about 600 rpm. About 2 grams of superabsorbent material to be tested was added into the beaker and a timer, available from Sper Scientific, Model 810026, was immediately started to record Gelation Time. Gelation Time is defined as the time when the superabsorbent material absorbs almost all the water; when the water mixture stops rotating within the beaker and looks like a whole piece of gel. The Gelation Time of each superabsorbent material was then measured and recorded. Table 1 summarizes the parameters and results of Gelation Time testing. Superabsorbent materials having a Gelation Time of greater than 40 seconds are typically able to make uniform absorbent foams and are useful in embodiments of this invention.

Each of the superabsorbent materials was then made into a freeze dried foam by the following procedure for the purpose of visually testing uniformity. After each slurry was poured into its respective pan the slurry was visually inspected for uniformity. A uniform foam sheet would appear relatively smooth and planar and have relatively few material conglomerates in the pan. A non-uniform sheet will typically have material conglomerates, due to the rapid absorption of slurry solvent by the superabsorbent material, that results in a relatively lumpy sheet with inconsistent material concentrations throughout the sheet. For each superabsorbent material, 1000 g of distilled water and 20 g of eucalyptus wood pulp fluff were added into a one gallon Hobart® mixer, model N50, manufactured by Hobart Canada, New York, Ontario, Canada. The fluff was mixed with the water by the stirrer of the mixer at a relatively slow speed (setting 1). 1.25 g of carboxymethyl cellulose, available from Aqualon Company, Wilmington, Del., designated as Cellulose Gum CMC-7H, was used as a binding agent and slowly added to the stirring slurry. After about 15 minutes of stirring, 10 g of the superabsorbent material, having a particle size ranging from about 300 μm to 600 μm, was added to the slurry while the stirrer of the mixer is mixing at a relatively fast speed (setting 2). The mixing is continued for about 10 seconds and the slurry was poured into a stainless steel pan with a size of 10×20×1 inches. The slurries containing a fast superabsorbent material with a Gelation Time of less than 40 seconds, were not able to form a uniform sheet in the pan. The slow superabsorbent material slurries and the fast superabsorbent material slurries containing enough binding agent to raise the Gelation Time over 40 seconds, did create uniform sheets in the pans. The pan was placed into a VirTis Genesis freeze dryer (Model 25 EL) made by The VirTis, Inc. And the temperature of the solutions were slowly cooled down to about −25° C. at a rate of about 0.1° C./minute. After an hour the condenser was turned on and when the temperature of the condenser reached −60° C. the vacuum pump was switched on. Vacuum reading of the dryer has to be below 200 millitorrs to ensure an effective drying rate. It took about at least 15 hours to completely dry the mixture.

TABLE 1

| SAM | SAM weight (g) | Binding Agent CMC (g) | Water Amount (g) | Water Temp. (° C.) | Gelation Time(s) | Uniformity? |
|---|---|---|---|---|---|---|
| DOW 2035 | 2 | 0 | 50 | 23 | 39 | No |
| Favor 880 | 2 | 0 | 50 | 23 | 31 | No |
| Favor 880 | 1.98 | 0.02 | 50 | 23 | 34 | No |
| Favor 880 | 1.96 | 0.04 | 50 | 23 | 36 | No |
| Favor 880 | 1.94 | 0.06 | 50 | 23 | 53 | Yes |
| Favor 880 | 1.90 | 0.10 | 50 | 23 | 87 | Yes |
| Favor 880 | 1.80 | 0.20 | 50 | 23 | 204 | Yes |
| Polyacrylic acid/NaHCO$_3$ | 2 | 0 | 50 | 23 | 375 | Yes |
| Favor 880 | 2 | 0 | 50 | 2 | 130 | N/A |
| Favor 880 | 2 | 0 | 50 | 42 | 13 | N/A |
| Favor 880 | 2 | 0 | 50 | 63 | 9 | N/A |

EXAMPLE 2

Table 2 summarizes sample compositions for Samples 1–5 and two control samples. To make each of the samples, 1000 g of distilled water and certain amounts of eucalyptus wood pulp fluff were added into a one gallon Hobart® mixer. The fluff was mixed with the water by the stirrer of the mixer at a relatively slow speed (setting 1). Carboxymethyl cellulose, available from Aqualon Company, designated as Cellulose Gum CMC-7H, was used as a binding agent and slowly added to the stirring slurry. After about 15 minutes of stirring, a superabsorbent powder having a particle size ranging from about 300 μm to 600 μm, available from Stockhausen Inc., designated as Favor 880, was added to the slurry while the stirrer of the mixer is on at a relatively fast speed (setting 2). The mixing is continued for about 20 seconds and the slurry was poured into a stainless steel pan with a size of 10×20×1 inches. The pan was placed into a VirTis Genesis freeze dryer, Model 25 EL from The VirTis, Inc., and the temperature of the solutions were slowly cooled down to about −25° C. at a rate of about 0.1° C./minute. After an hour the condenser was turned on and when the temperature of the condenser reached −60° C. the vacuum pump was switched on. Vacuum reading of the dryer has to be below 200 millitorrs to ensure an effective drying rate. It took about at least 15 hours to completely dry the mixture. The foams were then heated at 130° C. for 2 hours and subjected to testing. Non-foam control samples of uncreped through-air-dried (UCTAD) wood pulp fiber material and a bonded carded web ("Surge Material") of a composition comprising polypropylene (PP) and poly(ethylene terephthalate) (PET) were tested along side Samples 1–5. Table 2 summarizes the compositions of Samples 1–5 and the density and basis weights of all samples. Samples 1 and 2 are not foams of this invention, do not include superabsorbent material, and are prior art absorbent foams.

TABLE 2

| Sample No. | Polymer | Fluff percent | SAM percent | Density (g/cc) | Basis Weight (gsm) |
|---|---|---|---|---|---|
| 1 | 100% CMC | 0% | 0% | 0.018 | 100 |
| 2 | 4% CMC | 96% | 0% | 0.057 | 226 |
| 3 | 4% CMC | 77% | 19% | 0.047 | 270 |
| 4 | 4% CMC | 62% | 34% | 0.044 | 280 |
| 5 | 4% CMC | 48% | 48% | 0.044 | 230 |
| UCTAD | 100% sulfonated cellulose | 100% | 0% | 0.113 | 100 |
| Surge Material | 100% PP/PET | 0% | 0% | 0.022 | 90 |

Absorbency tests were performed by cutting the absorbent composites into circular disks with a diameter of 1 inch. About 0.16 g of foam discs of each sample were weighed and placed into a plastic absorbency under load (AUL) test cylinder with a 100 mesh screen on its bottom. For testing of absorbency under zero load (AUZL), a plastic piston was placed on the top of the discs which generated a pressure of about 0.01 psi. The cylinder with a foam disc was placed into a dish which contains about 50 ml of 0.9% by weight sodium chloride solution. After one hour, the cylinder was taken out and placed on paper towels to blot the interstitial fluid of the mesh. The blotting was continued by moving the cylinder to the area with dry paper towel until there was no fluid mark visible on the paper towel. The weight difference of the cylinder between wet and dry represents total amount of fluid absorbed by the foam and is used to calculate absorbency under zero load. In absorbency under load (AUL) testing at 0.3 psi, the test is the same except for an additional 100 g weight was applied on the top of the plastic piston.

Table 3 summarizes the results of the absorbency tests testing absorbency under zero load (AUZL) and AUL. Fibrous absorbent foams of this invention have an AUZL value, of at least 10 g liquid/g composite.

TABLE 3

| Sample No. | AUZL (g/g) | AUL @ 0.3 psi (g/g) |
|---|---|---|
| 1 | 26.1 | 18.3 |
| 2 | 13.4 | 8.6 |
| 3 | 13.6 | 10.3 |
| 4 | 16.8 | 11.7 |
| 5 | 19.6 | 13.9 |
| UCTAD | 5.2 | 4.5 |
| Surge Material | 2.8 | 2.2 |

A vertical liquid flux at different height of the samples was determined according to the procedure described below. A strip of each sample, having a width of about 5.08 cm and a length of about 38.1 cm, was obtained by using a textile saw, available from Eastman, Machine Corp., Buffalo, N.Y. The sample strip was cut at least about 2.54 cm away from the edge of the absorbent composite so as to avoid edge effects. The apparatus for holding a sample material while measuring the vertical liquid flux values for the sample absorbent composites consists of male and female halves. The apparatus has a length of about 21 inches and consists of glued Plexiglas. Small nails are placed about one inch apart in a bar of the male half. The female half has holes drilled to accommodate the nails. A size 4 mesh nylon screen was stretched onto the nails. The screen was about one inch shorter than the sample holder at both ends. Reinforcing plates stiffened the bar, preventing the bar from buckling under the tension from the nylon screen. Short, flat, perpendicular bars act as springs to stretch the nylon screen and to keep the sample in place.

The sample strip was placed on the nylon screen, with a bottom end of the sample strip placed lower than a bottom edge of the sample holder such that when the sample strip is positioned on the top of a liquid distribution manifold at the beginning of the experiment, the bottom of the sample strip will just touch the liquid surface. A second size 4 mesh nylon screen was stretched and placed on top of the sample strip. Two steel pins were driven through the sample strip at each of 5, 10, 15, and 30 centimeters from the bottom of the sample strip to prevent the movement of the sample strip under the weight of absorbed liquid. The female half of the sample holder was fitted onto the male half. Binder clips were used to keep the assembled holder together. During the evaluation, the sample strip and the sample holder were contained in a Plexiglas tubular enclosure having an inner diameter of about 18.42 cm and a height of about 60.96 cm. There is a slit (about 0.64 cm by about 7.62 cm) in the bottom of the tubular enclosure large enough to allow the tube from the aspirator bottle to the liquid distribution manifold to go through. The tubular enclosure was covered with a flat piece of Plexiglas. Distilled water was sprayed on the walls of the tubular enclosure before the experiment to raise the relative humidity inside the tubular enclosure so as to reduce the evaporation of water from the sample strip during the evaluation. The relative humidity should be maintained at about 90 to about 98 relative humidity during the evaluation. The liquid distribution manifold and the tubular enclosure rest on the top of a Plexiglas plate resting on two lab jacks used for adjustability, stability, and maintaining level. The aspirator bottle was filled with a 0.9% by weight sodium chloride aqueous solution. The solution in the aspirator bottle was in equilibrium with the upper edge of the slit in the bottom of the tubular enclosure. The scale was tared. The sample bolder was placed on the top of the liquid distribution manifold. A stopwatch was started as soon as the bottom edge of the sample strip touched the surface of the solution. The cover was placed on the top of the tubular enclosure.

The vertical distance of the liquid front traveling up the sample strip and the liquid weight absorbed by the sample strip at various times was recorded. The time versus liquid front height was plotted to determine the wicking time at about 5 centimeters and at about 15 centimeters. The weight of the liquid absorbed by the sample strip from the beginning of the evaluation to about 5 centimeters and to about 15 centimeters height was also determined from the data. The vertical liquid flux value of the sample strip at a particular height was calculated by dividing the grams of liquid absorbed by the sample strip by each of: the basis weight, in grams per square meter, of the sample strip; the time, in minutes, needed by the liquid to reach the particular height; and the width, in inches, of the sample strip.

Table 4 summarizes the results of a vertical wicking test. All embodiments of this invention have a vertical wicking height of at least 10 cm. Flux is reported in units of $1 \times 10^{-4}$ grams/gram per square meter/inch/minute. "N.A." means no fluid reached the height.

TABLE 4

| Sample | Zero Level Vertical Wicking | | | Wicking Capacity |
|---|---|---|---|---|
| No. | Flux @ 5 cm | Flux @ 10 cm | Flux @ 15 cm | (g/g) |
| 1 | 34.62 | 2.31 | N.A. | 5.8 |
| 2 | 258.21 | 54.75 | 7.25 | 9.8 |
| 3 | 167.06 | 29.28 | 10.53 | 9.2 |
| 4 | 149.79 | 23.64 | 6.49 | 9.4 |
| 5 | 70.85 | 9.84 | N.A. | 8.9 |
| UCTAD | 387.10 | 67.51 | 25.39 | 3.9 |
| Surge Material | N.A. | N.A. | N.A. | 0.9 |

A fluid intake test was performed on the samples by cutting the samples into 11.43 cm squares. A modified Mini-FIFE testing apparatus was used to evaluate fluid intake properties of the samples. One sample square was placed in the apparatus and 15 ml of 0.9% by weight sodium chloride solution was added into the center of the square through the filling hole of the apparatus. After ten minutes another 15 ml of sodium chloride solution was added. Sodium chloride solution was added until the fluid ran into the area outside of the 4.5 inch square testing area. The total amount of sodium chloride solution used before failure is used to derive into a fluid intake capacity parameter by dividing the amount by the weight of the dry sample.

Table 5 summarizes the results from the intake test. The intake test was performed at 6 insults of 15 ml at 10 minute intervals. The superscript "L" means that leakage occurred at that insult. Intake capacity for all sample of the fibrous absorbent foam according to this invention were greater than 15 g liquid/g composite.

TABLE 5

| Sample No. | Intake Time (sec) @ 15 ml/10 Minutes | | | | | | Intake Capacity (g/g) |
| --- | --- | --- | --- | --- | --- | --- | --- |
| | 1st | 2nd | 3rd | 4th | 5th | 6th | |
| 1 | 3.5 | 25.8 | 57.8$^L$ | | | | 11.2 |
| 2 | 1.7 | 0.9 | 2.5 | 18.4$^L$ | | | 17.8 |
| 3 | 1.3 | 5.9 | 11.6 | 26.7 | 45.8$^L$ | | 19.0 |
| 4 | 1.5 | 6.2 | 13.0 | 24.8 | 49.7$^L$ | | 21.5 |
| 5 | 0.9 | 3.3 | 10.3 | 18.2 | 27.5 | 41.4$^L$ | 24.5 |
| UCTAD | 5.4 | 56.3$^L$ | | | | | 7.1 |
| Surge Material | 0.6 | 0.8 | 0.8 | 0.8 | 0.8$^L$ | | 31.2 |

EXAMPLE 3

To demonstrate the increased intake rate and liquid lock-up characteristics of this invention five additional samples of freeze-dried foams were made. Table 6 summarizes the compositions of each freeze-dried foam sample made by the following process. For each sample an amount of distilled water listed in Table 6 was poured into a 4 liter Hobart® mixer, Model N50, manufactured by Hobart Canada, North York, Ontario, Canada. The mixer has 3 mixing settings. The mixer was initially set at a relatively slow mixing rate (the first setting) and, while stirring, an amount of wood pulp fluff, available from US Alliance Coosa Pines Corporation, Alabama, designated CR-1654, listed in Table 6 was added to the appropriate water amount. Then the appropriate amount of binder material from Table 6, carboxymethyl cellulose, available from Aqualon Company, Wilmington, Del., designated CMC-7H, was slowly added into the mixer. The addition of the binder material was slow enough to prevent agglomeration of the carboxymethyl cellulose powder.

After mixing for about two minutes, the mixer speed was increased to the second mixing setting. After mixing for an additional five minutes at the faster speed the superabsorbent material, Drytech 2035, available from Dow Chemical Company, Midland, Mich., was added into the mixer and mixed for about 10 seconds at the same mixing speed. The resulting uniform slurries for each sample were each poured into a separate 25.6 cm wide, 51.2 cm long, and 5.2 cm deep stainless steel pan. Each pan was put into a VirTis Genesis Freeze Dryer, Model 25 EL, manufactured by VirTis, Gardiner, N.Y. The samples were freeze dried in the freeze dryer at a shelf temperature of below −50° C., a condenser temperature of below −70° C., and a vacuum of less than 100 militorrs. The samples were freeze-dried between 2 to 3 days depending upon the total loading of frozen water in the dryer. The freeze-dried foam samples were then heat treated at 130° C. for two hours to insolubilize the binder material.

TABLE 6

| Sample No. | Superabsorbent Material (g) | Wood Pulp Fluff (g) | Binder Material (g) | Water (g) |
| --- | --- | --- | --- | --- |
| 6 | 28.3 | 28.3 | 6.3 | 1500 |
| 7 | 28.3 | 28.3 | 6.3 | 2000 |
| 8 | 28.3 | 28.3 | 6.3 | 2500 |
| 9 | 16.8 | 39.8 | 6.3 | 1500 |
| 10 | 39.8 | 16.8 | 6.3 | 1500 |

Figure 5B:
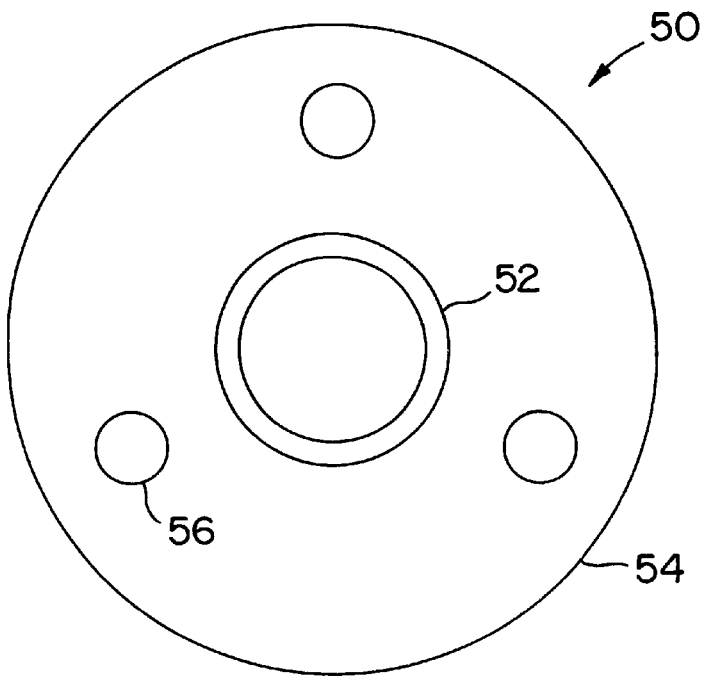
FIG. 5B is a top view of the intake rate testing device.
Figure 5A:
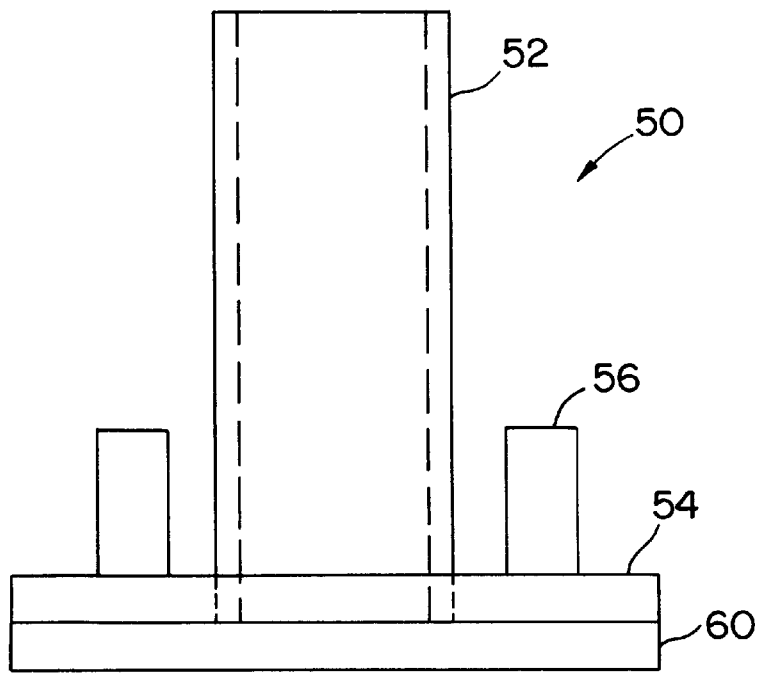
FIG. 5A is a plan view of an intake rate testing device.

Intake rate is determined by pre-weighing a 7.68 cm diameter sample of each of Samples 6–10, and placing the 7.68 cm diameter sample under a cylindrical port device as shown in FIGS. 5A and 5B. FIG. 5A shows cylindrical port device 50 having cylinder 52 and base 54. Cylindrical port device 50 can be made from various material, such as plastic, and has a weight that will result in pressure being placed on sample 60 below the cylindrical port device 50. As shown in FIG. 5B, additional weights 56 can be placed on base 54 for testing sample 60 at higher pressures. Sample 60 has a diameter substantially equal to the diameter of base 54, which is 7.68 cm for each in the present testing, and is placed under base 54 during testing. The cylindrical port device used in testing Samples 6–10 was made of plastic having a weight of about 39 grams. Additional weights 56, totaling 250 grams, were added to obtain a testing pressure on the samples of about 0.09 pounds per square inch (psi).

Cylinder 52 is hollow with an inner diameter of 2.54 cm, allowing for liquid to be poured into cylinder 52 and contact sample 60 below. For Samples 6–10, 15 cubic centimeters (cc) of 0.9% by weight sodium chloride solution is poured into the cylindrical port device. The time required for the volume of liquid to be absorbed into the samples at the base of the device is recorded. Divide the total charge of 15 cc by the intake time for each sample to obtain the intake rate for that sample.

Figure 6:
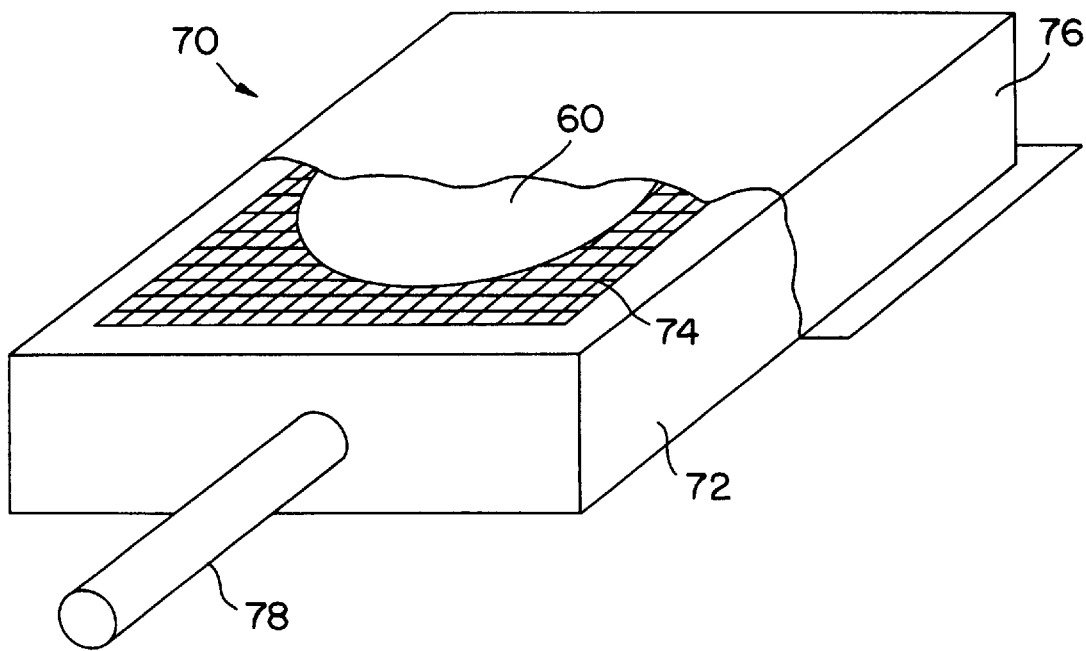
FIG. 6 is a perspective view of a liquid lock-up testing apparatus.

A typical vacuum apparatus useful for lock-up testing is shown in FIG. 6. Vacuum apparatus 70 has base 72 with mesh screen 74 and vacuum tube 78 attached to a vacuum source. Sample 60 is placed onto mesh screen 74, typically a size 100 mesh screen, and sample 60 and base 72 are covered by gas impervious rubber dam 76. A vacuum is applied through vacuum tube 78 and, because rubber dam 76 creates a seal around base 72, the vacuum pulls an amount of liquid from sample 60. The amount of fluid collected in base 72 is measured. The amount of fluid maintained by sample 60 is determined by obtaining the net weight of the sample by subtracting the dry weight of the material from the wet weight of the material after application of the vacuum, and converting the net weight to milliliters using the density of the test liquid.

For Samples 6–10, lock-up testing is done following the intake rate test by waiting 60 seconds, putting each sample absorbent composite on a vacuum apparatus and applying a vacuum of about 13.5 psig for two minutes. After applying vacuum for 60 seconds, the mass of sodium chloride solution left in the sample was determined. Determine liquid lock-up by dividing the mass of liquid remaining in the sample by the total initial insult.

The intake and lock-up tests are repeated for each of Sample 6–10 three times for a total insult of 45 cc sodium chloride solution applied to the sample. After the lock-up testing of each sample, however, the sample composite has been drained of some of the liquid from the intake rate testing insult. Therefore, for the second intake and lock-up tests a new (although same in composition) sample is used. The second, identical sample is given a first 15 cc insult of 0.9% by weight sodium chloride solution insult (equivalent to the amount from the first intake rate test) and, after waiting 15 minutes, a second 15 cc insult of 0.9% by weight sodium chloride solution, for a total of 30 cc of 0.9% by weight sodium chloride solution. After the second intake rate test a second lock-up test is performed, so the third intake rate test also uses a new, nominally identical sample. The third, identical sample is given a first 15 cc insult of 0.9% by weight sodium chloride solution (equivalent to the amount from the first intake rate test), a second of 15 cc insult of 0.9% by weight sodium chloride solution after 15 minutes, and, after waiting an additional 15 minutes, a third 15 cc insult of 0.9% by weight sodium chloride solution is added to the sample for a total of 45 cc of 0.9% by weight sodium chloride solution.

The calculations for intake rate are the same each time. To calculate lock-up on subsequent insults, divide the cumulative mass of liquid remaining in the sample after vacuum by the cumulative amount of liquid that has been added to the sample. When the intake rate and lock-up tests are complete a saturation test was conducted on a nominally identical sample to determine total saturation capacity of the superabsorbent material.

The saturation capacity of a superabsorbent material or insoluble fiber is determined by a centrifuge retention capacity test. The Centrifugal Retention Capacity (CRC) is a measure of the absorbent capacity of a sample after being subjected to centrifugation under controlled conditions. The samples are placed between two Teflon coated fiberglass screens having ¼ inch openings (Taconic Plastics, Inc., Petersburg, N.Y.) and submerged in a pan of 0.9% by weight sodium chloride solution making sure that the screens are held down until the samples are completely wetted. After wetting, the samples remain in the solution for 30 minutes, at which time they are removed from the solution and temporarily laid on a nonabsorbent flat surface. The samples are then placed into the basket of a suitable centrifuge capable of subjecting the samples to a g-force of 350. One suitable centrifuge is a Heraeus Instruments Labofuge 400, having a water collection basket, digital rpm gauge, and machined drainage basket adapted to hold and drain the samples. The samples must be placed in opposing positions within the centrifuge to balance the basket when spinning. The samples were centrifuged at 1600 rpm to achieve the targeted g-force of 350, for 3 minutes. The samples are removed and weighed. All fluid not locked-up (absorbed) in the superabsorbent material is centrifuged out of the sample. The amount of fluid absorbed and retained by the superabsorbent material is the centrifuge retention capacity of the superabsorbent material, expressed as grams of fluid per gram of superabsorbent material. The centrifuge retention capacity (in grams of fluid per grams of superabsorbent material) of Samples 6–10 was 30 cc/cc.

Because intake rate and liquid lock-up fraction change as a function of saturation, the data should be normalized to a common set of criteria. Using the saturated capacity of the composite, determine the percent saturation of sample upon each insult. For example, a 15 cc insult to a sample with a 45 cc saturation capacity yields 33% saturation. Plot the intake rate of an absorbent composite as a function of the percent saturation. Interpolate the effective intake rate at the 80% composite saturation level. For interpolation, the intake rate data are plotted against the respective composite saturation percent in a scatter plot with smoothed lines using the spreadsheet Microsoft Excel 97®. To determine the intake rate at 80% composite saturation, a line is drawn along the scatter plot parallel to the y-axis at 80% composite saturation. The intake rate is then determined from the scatter plot at the point where the line intersects the curve.

Liquid lock-up fractions are also normalized. Rather than normalizing to the composite saturation level, however, the lock-up fractions are normalized to the saturation capacity of the superabsorbent material alone. This is done to better reflect the ability of the superabsorbent material to lock-up liquid relative to the superabsorbent material total saturation capacity.

The lock-up fraction at 50% superabsorbent saturation is determined by plotting the lock-up fraction test data against the superabsorbent material saturation and then interpolating the value from the plot. Lock-up fraction is equal to the amount of liquid in the sample after vacuuming divided by the cumulative insult amount. As the matrix fibers of the composite also absorb a small amount of fluid this absorption, as determined by the centrifuge retention capacity test, will be taken into account in the calculations. Superabsorbent saturation is determined according to the following formula.

$$\text{Superabsorbent Saturation} = \frac{(A) - (B)(C)(D)}{(B)(E)(F)}$$

Where "A" is the amount of liquid in the composite after vacuum, "B" is the composite dry mass, "C" is the fiber fraction, "D" is the typical intrafiber absorption capacity, "E" is the superabsorbent fraction, and "F" is the centrifuge retention capacity of the composite. The fiber fraction is the total composite fiber weight divided by the total composite weight. Likewise the superabsorbent fraction is the total superabsorbent material weight divided by the total composite weight.

For interpolation, the lock-up fraction data are plotted against the respective superabsorbent material saturation percent in a scatter plot with smoothed lines using the spreadsheet Microsoft Excel 97®. To determine the lock-up fraction at 50% superabsorbent saturation, a line is drawn across the scatter plot parallel to the y-axis at 50% superabsorbent saturation. The lock-up fraction is then determined from the scatter plot at the point where the line intersects the curve.

Samples 6–10 were tested by the intake rate test and lock-up test. The results of testing three replicate samples are averaged and summarized in Table 7. Samples 6–9 all have both the desired intake rate and lock-up characteristics taught by this invention. Freeze-dried foam Sample 10, which had a 60% superabsorbent level, did not have the intake rate and lock-up characteristics of this invention. Table 7 shows the superabsorbent material of the samples as a percentage of the weight of fiber/superabsorbent material. The liquid lock-up numbers in Table 7 are at a 50% superabsorbent material saturation and the intake rates are at 80% absorbent composite saturation.

TABLE 7

| Sample | Structure | Superabsorbent Material (%) | Liquid Lock-up | Intake Rate (cc/s) |
|---|---|---|---|---|
| 6 | Freeze-dried foam | 50 | 0.83 | 6.2 |
| 7 | Freeze-dried foam | 50 | 0.82 | 3.3 |
| 8 | Freeze-dried foam | 50 | 0.81 | 3.6 |
| 9 | Freeze-dried foam | 30 | 0.78 | 14.1 |
| 10 | Freeze-dried foam | 60 | 0.90 | 0.40 |

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent fibrous foam, comprising:
   a water insoluble fiber; and
   a superabsorbent material;
   wherein the absorbent fibrous foam comprises a fluid intake capacity of at least 15 g/g, a vertical wicking distance of at least 10 cm, and an absorbency under zero load of at least 15 g/g.

2. The absorbent fibrous foam of claim 1, comprising about 10 to 80 weight percent of superabsorbent material, wherein weight percent is based on total weight of the absorbent fibrous foam.

3. The absorbent fibrous foam of claim 2, comprising about 20 to 70 weight percent of superabsorbent material, wherein weight percent is based on total weight of the absorbent fibrous foam.

4. The absorbent fibrous foam of claim 3, comprising about 30 to 60 weight percent of superabsorbent material, wherein weight percent is based on total weight of the absorbent fibrous foam.

5. The absorbent fibrous foam of claim 1, comprising about 20 to 90 weight percent of water-insoluble fiber, wherein weight percent is based on total weight of the absorbent fibrous foam.

6. The absorbent fibrous foam of claim 5, comprising about 30 to 80 weight percent of water-insoluble fiber, wherein weight percent is based on total weight of the absorbent fibrous foam.

7. The absorbent fibrous foam of claim 6, comprising about 40 to 70 weight percent of water-insoluble fiber, wherein weight percent is based on total weight of the absorbent fibrous foam.

8. The absorbent fibrous foam of claim 1, further comprising a binding agent.

9. The absorbent fibrous foam of claim 8, comprising about 0 to 20 weight percent of binding agent, wherein weight percent is based on total weight of the absorbent fibrous foam.

10. The absorbent fibrous foam of claim 9, comprising about 2 to 10 weight percent of binding agent, wherein weight percent is based on total weight of the absorbent fibrous foam.

11. The absorbent fibrous foam of claim 1, wherein the foam comprises a density of less than about 0.1 grams foam/cubic centimeter foam.

12. The absorbent fibrous foam of claim 11, wherein the foam comprises a density of about 0.01 to 0.1 grams foam/cubic centimeter foam.

13. The absorbent fibrous foam of claim 1, wherein the foam is a densified foam comprising a density of about 0.2 to 0.5 grams foam/cubic centimeter foam.

14. A method of producing a low-density absorbent fibrous composite, comprising the steps of:
forming a slurry comprising water and a water-insoluble fiber;
adding an absorbent material having a Gelation Time of at least 40 seconds to the slurry;
cooling the slurry to a temperature between about −70° C. and 0° C. at a cooling rate effective to freeze the water;
substantially removing the frozen water from the slurry; and
recovering an absorbent fibrous foam.

15. The method of claim 14, wherein the slurry comprises about 1 to 10 weight percent of the water-insoluble fiber, based on total solution weight.

16. The method of claim 14, further comprising about 0.001 to 5 weight percent of a binding agent, based on total solution weight.

17. The method of claim 14, wherein the absorbent material comprises a water-swellable, water-insoluble superabsorbent material.

18. The method of claim 17, wherein the absorbent fibrous foam comprises about 10 to 80 weight percent superabsorbent material, based on total weight of the absorbent fibrous foam.

19. The method of claim 18, wherein the absorbent fibrous foam comprises about 20 to 70 weight percent superabsorbent material, based on total weight of the absorbent fibrous foam.

20. The method of claim 19, wherein the absorbent fibrous foam comprises about 30 to 60 weight percent superabsorbent material, based on total weight of the absorbent foam.

21. The method of claim 14, wherein the absorbent fibrous foam comprises water-insoluble fiber in a weight amount of about 20 to 90 weight percent, based on total weight of the absorbent fibrous foam.

22. The method of claim 21, wherein the absorbent fibrous foam comprises about 30 to 80 weight percent water-insoluble fiber, based on total weight of the absorbent fibrous foam.

23. The method of claim 22, wherein the absorbent fibrous foam comprises about 40 to 70 weight percent water-insoluble fiber, based on total weight of the absorbent fibrous foam.

24. The method of claim 16, wherein the absorbent fibrous foam comprises about 0 to 20 weight percent binding agent, based on total weight of the absorbent fibrous foam.

25. The method of claim 24, wherein the absorbent fibrous foam comprises about 2 to 10 weight percent binding agent, based on total weight of the absorbent fibrous foam.

26. The method of claim 14, wherein the absorbent fibrous foam has a fluid intake capacity of at least 15 g/g, a vertical wicking distance of at least 10 cm, and an absorbency under zero load of at least 15 g/g.

27. The method of claim 14, wherein the superabsorbent material comprises at least one of a crosslinked anionic and cationic polymer selected from the group consisting of sodium-polyacrylates, carboxymethyl celluloses, carboxymethyl polysaccharides, polyaspartic acid salts, maleic anhydride-isobutylene copolymers, chitosan salts, polyquarternary ammonium salts, polyvinyl amines, and combinations thereof.

28. The method of claim 17, wherein the superabsorbent material comprises a coating of a hydrophobic agent.

29. The method of claim 28, wherein the superabsorbent material comprises a form selected from the group consisting of particles, fibers, filaments, nonwovens, coforms, printings, coatings, and combinations thereof.

30. The method of claim 28, wherein superabsorbent material comprises at least one of a superabsorbent particle and superabsorbent fiber having a diameter of about 100 microns to 1000 microns.

31. The method of claim 28, wherein the superabsorbent material comprises a nonionic, non-neutralized polymer superabsorbent material.

32. The method of claim 28, wherein the superabsorbent material comprises a coating of a nonabsorbent chemical.

33. The method of claim 28, wherein the superabsorbent material comprises a non-neutralized ion-exchanging superabsorbent material.

34. The method of claim 14, wherein the water in the slurry has an initial water temperature between about 4° C. to 23° C.

35. The method of claim 34, wherein the initial water temperature is about 10° C. to 23° C.

36. The method of claim 14, wherein the water-insoluble fiber comprises at least one of a natural fiber and a synthetic fiber.

37. The method of claim 36, wherein the water-insoluble fiber is selected from the group consisting of wood pulp fibers, cotton linter, thermoplastic fibers, elastic fibers, rayon fibers, and combinations thereof.

38. The method of claim 37, wherein the thermoplastic fiber is selected from the group consisting of polyethylene, polypropylene, poly(ethylene terephthalate), and combinations thereof.

39. The method of claim 36, wherein the synthetic fibers are selected from the group consisting of polyvinyl alcohol, polyvinyl chloride, polyacrylonitrile, polyurethane, and combinations thereof.

40. The method of claim 36, wherein the water-insoluble fiber comprises a hydrophilic fiber.

41. The method of claim 40, wherein the hydrophilic water-insoluble fiber comprises a surface treated hydrophobic fiber.

42. The method of claim 36, wherein a fiber diameter of the water-insoluble fiber has a diameter of about 1 to 100 microns.

43. The method of claim 42, wherein the fiber diameter of the water-insoluble fiber is about 1 to 50 microns.

44. The method of claim 43, wherein the fiber diameter of the water-insoluble fiber is about 1 to 30 microns.

45. The method of claim 16, wherein the binding agent is water-soluble before adding the superabsorbent material and water-insoluble after recovering the absorbent fibrous foam.

46. The method of claim 16, wherein the binding agent comprises a polymer having a molecular weight of about 10,000 to 10,000,000.

47. The method of claim 46, wherein the polymer has a molecular weight of about 100,000 to 1,000,000.

48. The method of claim 45, further comprising the step of adding a crosslinking agent to the slurry.

49. The method of claim 14, wherein the temperature is between about −70° C. and −30° C.

50. The method of claim 49, wherein the temperature is between about −70° C. to −40° C.

51. The method of claim 50, wherein the temperature is between about −70° C. to −50° C.

52. The method of claim 14, wherein the cooling rate is slower than a critical cooling rate.

53. The method of claim 52, wherein the cooling rate is about 0.01° C./minute to 10° C./minute.

54. The method of claim 14, further comprising the step of crosslinking the absorbent fibrous foam.

55. An absorbent article comprising an absorbent fibrous foam prepared according to the method of claim 14.

56. The method of claim 14, wherein the foam comprises a density of less than about 0.1 grams foam/cubic centimeter foam.

57. The method of claim 56, wherein the foam comprises a density of about 0.01 to 0.1 grams foam/cubic centimeter foam.

58. The method of claim 56, further comprising densifying the absorbent fibrous foam.

59. The method of claim 58, wherein the densified absorbent fibrous foam comprises a density of about 0.2 to 0.5 grams foam/cubic centimeter foam.

60. A method of producing an absorbent fibrous composite, comprising the step of:
forming a slurry comprising water, a water-insoluble fiber, and a high molecular weight polymer binding agent;
adding a water-swellable, water-insoluble superabsorbent material having a Gelation Time of at least 40 seconds to the slurry;
cooling the slurry to a temperature between about −70° C. and 0° C. at a cooling rate effective to freeze the water;
substantially removing the frozen water from the slurry; and
recovering an absorbent fibrous foam.

61. The method of claim 60, wherein the slurry comprises about 1 to 10 weight percent of the water-insoluble fiber, based on total solution weight.

62. The method of claim 60, further comprising about 0.001 to 5 weight percent of a binding agent, based on total solution weight.

63. The method of claim 60, wherein the absorbent fibrous foam comprises a fluid intake capacity of at least 15 g/g, a vertical wicking distance of at least 10 cm, and an absorbency under zero load of at least 15 g/g.

64. The method of claim 60, wherein the superabsorbent material has at least one of a crosslinked anionic and cationic polymer selected from the group consisting of sodium-polyacrylates, carboxymethyl celluloses, carboxymethyl polysaccharides, polyaspartic acid salts, maleic anhydride-isobutylene copolymers, chitosan salts, polyquartemary ammonium salts, polyvinyl amines, and combinations thereof.

65. The method of claim 60, wherein the binding agent comprises a polymer having a molecular weight of about 1,000 to 10,000,000.

66. The method of claim 65, wherein the polymer has a molecular weight of about 10,000 to 1,000,000.

67. The method of claim 60, further comprising the step of adding a crosslinking agent to the solution.

68. The method of claim 60, wherein the temperature is about −70° C. to −30° C.

69. The method of claim 68, wherein the temperature is about −70° C. to −40° C.

70. The method of claim 69, wherein the temperature is about −70° C. to −50° C.

71. The method of claim 60, wherein the cooling rate is slower than a critical cooling rate.

72. The method of claim 71, wherein the cooling rate is about 0.01° C./minute to 10° C./minute.

73. The method of claim 67, further comprising the step of crosslinking the absorbent fibrous foam.

74. A diaper comprising the absorbent fibrous composite produced according to the method of claim 60.

75. Training pants comprising the absorbent fibrous composite produced according to the method of claim 60.

76. Swim wear comprising the absorbent fibrous composite produced according to the method of claim 60.

77. An adult incontinence garment comprising the absorbent fibrous composite produced according to the method of claim 60.

78. A feminine hygiene product comprising the absorbent fibrous composite produced according to the method of claim 60.

79. A medical absorbent product comprising the absorbent fibrous composite produced according to the method of claim 60.

80. The method of claim 60, wherein the foam comprises a density of less than about 0.1 grams foam/cubic centimeter foam.

81. The method of claim 80, wherein the foam comprises a density of about 0.01 to 0.1 grams foam/cubic centimeter foam.

82. The method of claim 80, further comprising densifying the absorbent fibrous foam.

83. The method of claim 82, wherein the densified absorbent fibrous foam comprises a density of about 0.2 to 0.5 grams foam/cubic centimeter foam.

* * * * *